United States Patent [19]
Gilliard

[11] Patent Number: 5,255,688
[45] Date of Patent: Oct. 26, 1993

[54] INSTRUMENT FOR HANDLING BIOPSIES AND SPECIMENS

[75] Inventor: René Gilliard, Saint-Sulpice, Switzerland

[73] Assignee: Bredam Medical Distribution S.A., Switzerland

[21] Appl. No.: 679,063

[22] PCT Filed: Sep. 26, 1990

[86] PCT No.: PCT/CH90/00228
§ 371 Date: May 24, 1991
§ 102(e) Date: May 24, 1991

[87] PCT Pub. No.: WO91/04709
PCT Pub. Date: Apr. 18, 1991

[30] Foreign Application Priority Data
Sep. 27, 1989 [CH] Switzerland ............ 3504/89
Aug. 6, 1990 [CH] Switzerland ............ 2557/90

[51] Int. Cl.$^5$ ............................................. A61B 10/00
[52] U.S. Cl. ...................................... 128/753; 128/763
[58] Field of Search .............. 128/749, 752, 753, 758, 128/763, 765

[56] References Cited

U.S. PATENT DOCUMENTS

| | | | |
|---|---|---|---|
| 3,727,602 | 4/1973 | Hyden et al. | 128/753 |
| 3,943,917 | 3/1976 | Johansen | 128/763 |
| 4,366,822 | 1/1983 | Altshaler | 128/753 |
| 4,660,569 | 4/1987 | Etherington | 128/765 |
| 4,664,128 | 5/1987 | Lee | 128/763 |
| 4,967,762 | 11/1990 | De Vries | 128/753 |

*Primary Examiner*—Max Hindenburg
*Attorney, Agent, or Firm*—Woodard, Emhardt, Naughton, Moriarty & McNett

[57] ABSTRACT

The instrument for handling biopsies and specimens comprises a main body (3) the shape of which is similar to that of a syringe, a piston (4), a recoil means (7) and a portion (5) for contact with the specimen (2). In order that the degree of accomplishment of the suction effect caused by the action of the recoil means (7) shall not prejudice the ejection effect, a microchannel (8) as a calibrated air inlet enables the compensation of the deficit in volume when the specimen is obstructing the orifice (6) of the suction-ejection channel (10). Ejection of the specimen by airjet may thus take place in every case from a position of the piston corresponding with maximum volume.

3 Claims, 5 Drawing Sheets

INSTRUMENT FOR HANDLING BIOPSIES AND SPECIMENS

The present invention relates to an instrument for handling biopsies and specimens.

When a doctor is bent on knowing the nature of tissue in general he takes one or more specimens of it and then has them analysed Whatever the medical discipline in question actually is, the same type of problem is encountered when it is a question of manipulating specimens and biopsies. In fact specimens and biopsies have in general very little consistency and appear as small as sticky masses which adhere obstinately to the instrument which enables them to be taken. Depending upon the domain the manipulation is made still more difficult by reason of the very small size of the instruments taking the specimens and consequently of the specimens themselves.

In general the first phase of the manipulation consists in detaching the specimen from the instrument in order to deposit it in a bottle containing a preserving liquid, which bottle will then be dispatched to the laboratory for analysis. This first operation is in general effected while the patient is present and in the majority of cases the doctor reuses the same instrument for taking other specimens from the same patient. Under these conditions it is not possible to dip this instrument into the preserving liquid and shake it in it for the specimen to detach itself from the instrument. In fact it is out of the question to reuse an instrument contaminated with the preserving liquid. Moreover the preserving liquid would attack the instrument and rapidly render it unusable.

Hence of necessity the manipulation consists in holding the instrument containing or carrying the specimen above the bottle and trying to make the specimen fall into the bottle. In order to do this the operator utilizes a pointed instrument and unsticks the specimen by scratching it or scraping it. This method of proceeding has disadvantages of several orders. In the first place the specimen is often damaged, sometimes to such an extent that analysis is no longer even possible. A second disadvantage is that the cutting edge of the instrument, which is obviously essential, withstands this treatement poorly. A third disadvantage is that the doctor must in general wait for this operation to be finished and for his instrument to be returned to him for taking other specimens. The patient who is often placed in a not very comfortable situation does not particularly appreciate this enforced wait. In these last two cases the smaller or stickier the specimen the more difficult is the operation of transfer into the bottle and the longer the wait.

The same type of problem is likewise encountered in the analytical laboratories where the specimens also form the object of manipulations and transfers by the same means and with similar difficulties.

The aim of the present invention is to propose an instrument which enables the difficulties mentioned above to be met.

For this purpose the invention relates to an instrument for the handling of biopsies and specimens, characterized in that it includes pneumatic means for taking charge of the specimen.

Before starting the description of the several versions of the instrument in accordance with the invention, it is opportune to locate the particular technical problems which result from the very function of the instrument as well as from the setting in which it is intended to be used. In fact these problems are met again in the majority of the versions explained below.

It should be noted firstly that the user is in general holding another instrument in one of his hands. Consequently the transfer instrument should be able to be actuated by only one hand. That also means that the operator should be able to control with one hand and without difficulty the sequence of the suction effect and the ejection effet. In other words the instrument which by definition is self-contained should on its own allow the linking of these two phases without the step of accomplishing the first prejudicing the second.

The several versions of the instrument in accordance with the invention are described below and the reference numbers indicated refer to the drawing in which.

Figure 1:
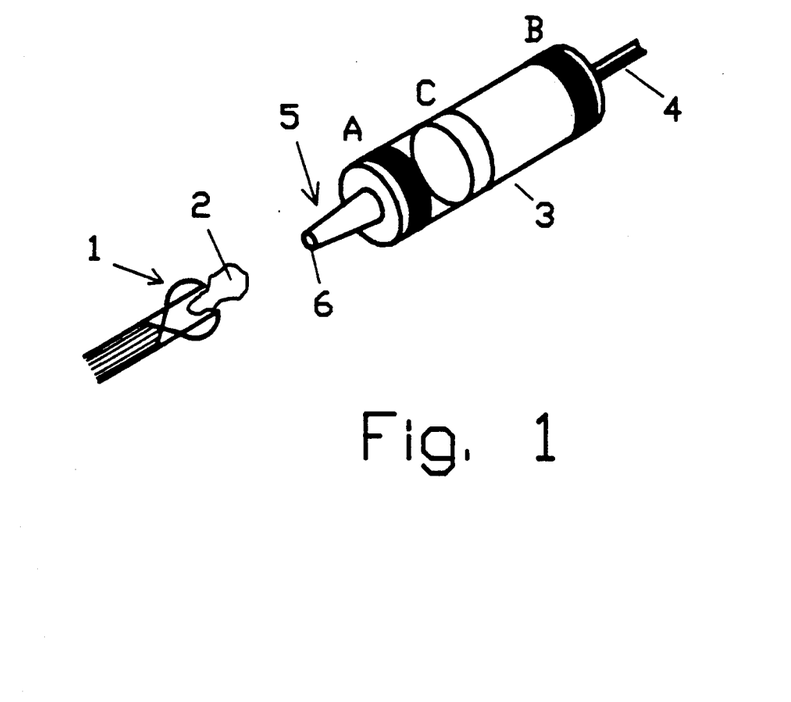
FIG. 1—shows a deliberately incomplete version of the instrument in order to illustrate by the drawing one of the problems with which the realization of the instrument is confronted.

In FIG. 1 a biopsy forceps is identified by 1, a specimen by 2, a chamber of variable volume by 3, a piston by 4 and the portion for contact between the specimen and the instrument by 5, in which the orifice 6 of the suction-ejection channel may be distinguished.

For a start the piston 4 is placed in the position A which indicates the state of minimum volume of the chamber of variable volume. A means of recoil not shown in this figure tends to push or draw the piston back towards the position B of maximum volume. The result is of course an effect of suction and the specimen sticks to the contact portion 5 and plugs the orifice 6 of the channel. This plugging occurs more or less quickly but in general well before the piston reaches the position B.

In order to get a clear picture let it be assumed that the piston stops in the intermediate position C. In fact if contact between the specimen and the contact portion 5 is perfect right from the start, plugging is immediate and the interval between position A and position C only conveys the ability of the contained air to expand. In this deliberately extreme case it will be understood that if pressure is exerted on the piston the return to position A will enable the contained air to recover its initial volume but no jet of air and no effect of ejection will result from it. The specimen which as already said is sticky, will remain stuck to the contact portion 5. In fact in order to produce a jet of air sufficient to eject the specimen it is necessary for the piston 4 to be able to recover the position B of maximum volume.

Figure 2:
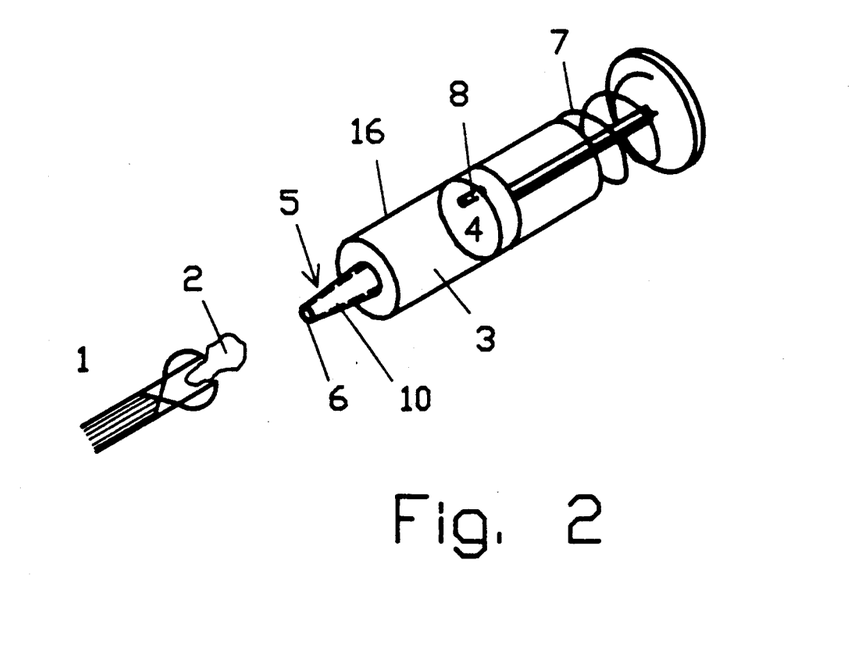
FIG. 2—illustrates diagrammatically in perspective a first version of the instrument.

FIG. 2 still shows the biopsy forceps 1, the specimen 2, the variable-volume chamber 3, the piston 4, the contact portion 5 and the orifice 6 of the channel. In addition the means of recoil 7 may be noticed, here represented by an external spring. It should be made clear in order not to come back to it again, that the spring may be placed inside the variable-volume chamber 3. In passing through the piston from side to side a microchannel 8 forms a calibrated air inlet. This microchannel may also be arranged at another point of the instrument, in particular next to the contact portion, the important thing being that this channel should open into the interior of the volume enclosed in the variable-volume chamber as it occurs when the piston is in its position of minimum volume.

Putting FIGS. 1 and 2 alongside, the development of the operations as described with respect to FIG. 1 is repeated. When the specimen 2 is obstructing the orifice 6 in the suction-ejection channel, the piston 4 no longer stops in the intermediate position C but under the action of the recoil means 7 it returns right to the position B of maximum volume thanks to the admission of air which passes through the microchannel 8.

When the piston has regained its position of maximum volume the specimen no longer undergoes any effect of suction but it adheres sufficiently to the contact portion of the instrument because it is sticky.

The area of the cross section of the microchannel is of first importance for the realization of the effect described. If the area is too large the effects of suction and ejection may be diminished to an extent which renders the instrument of little use. If on the contrary the area is too small the time necessary for the piston to regain the position of maximum volume may be drawn out considerably and render use of the instrument fussy. The ideal area must be sought by trial and error for it depends upon the respective dimensions that are chosen for all of the parts of the instrument.

Figure 3:
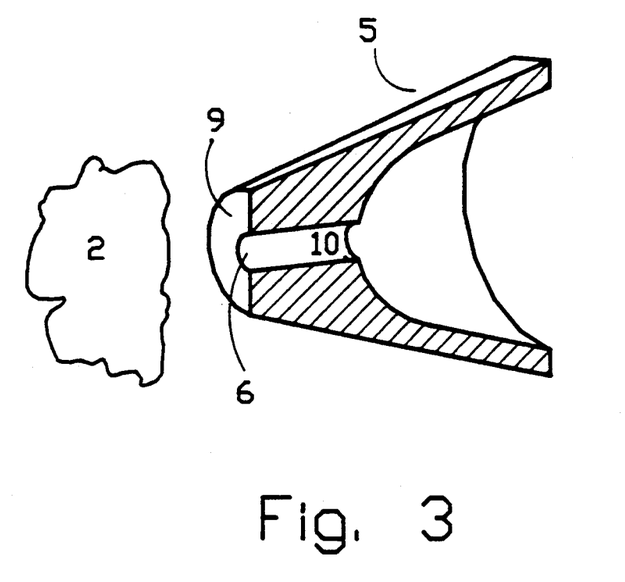
FIG. 3—illustrates in section a detail of one portion of the instrument, the portion intended for contact with the specimen.

In FIG. 3 may be seen the specimen 2 as well as the contact portion 5 of the instrument. The orifice 6 of the suction-ejection channel 10 may be noticed again. The proportions of the contact portion 5 and more especially the ratio between the area of contact 9 and the area of the orifice 6 of the suction-ejection channel are important for obtaining a good compromise, a good balance between the various effects of the instrument. The specimen being sticky, the greater the area of contact 9 the more the specimen will adhere to the instrument. This area may be increased or reduced depending upon whether it is fashioned like a tent or as a projecting dome or cone. In general tests show that the best results are obtained when the area of contact 9 lies in a plane normal to the longitudinal axis of the instrument.

As the specimens are produced by various instruments their size is of course variable. The statements which follow are given for a specimen produced by a biopsy forceps utilized in relation with a fibroscope or endoscope the working channel of which is 1,8 mm in area. For specimens of this type, for the circular area of contact 9 it is necessary to keep to a diameter of 1 mm and for the orifice 6 of the channel a diameter of 0,5 mm. These dimensions give rise to a ratio of about 3 to 1 between the real area of contact 9 and the area of the orifice 6. These proportions may be preserved in the realization of contact portions adapted to more voluminous specimens or to specimens which might be still smaller.

It is advisable to fashion the contact portion 5 as a cone which forms the tie between the contact area 9 and the main body 16 of the instrument consisting essentially of the chamber of variable volume. Fashioning in the shape of a cone in fact facilitates the positioning of the contact portion of the instrument, especially if it is a question of introducing it between the cups of a biopsy forceps.

The contact portion 5 of which the essential parts have just been described, is designated to be able to cooperate with the remainder of the instrument according to three modes. These three modes depend on the one hand upon the alternative concerning the disposable (single-use) or non-disposable character of the whole instrument and on the other hand, if the instrument is designated to be disposable, upon the question of knowing whether the contact portion may be provided in the injection moulding of the main body of the instrument or if on the contrary this contact portion should be attached to a main body already moulded.

If the instrument is disposable it is possible to employ installations for the manufacture of plastics syringes such as those which exist in numerous models on the market. In this case the instrument appears substantially as illustrated in FIG. 2, which corresponds with the first version of the instrument in accordance with the invention. In this case if the injection mould may be completed by the imprint of the contact portion 5 it is sufficient to refer to the described characteristics of the contact portion and to shape the imprint accordingly.

If on the contrary it is not possible to introduce the imprint of the contact portion into the injection mould, it is recommended that the contact portion be provided with a connecting member of male-female type which may be plugged permanently into the corresponding member of the main body of the instrument. In this respect it should be noted that plastics syringes have available all such arrangements by reason of the fact that they are intended for collaborating with needles which bear complementary arrangments.

If the instrument is not designated to be disposable the contact portion includes a coupling zone corresponding with the standard connection retained for the corresponding portion of the instrument. The contact portion then occurs in the form of a removable tip and is described below by reference to FIG. 4.

Figure 4:
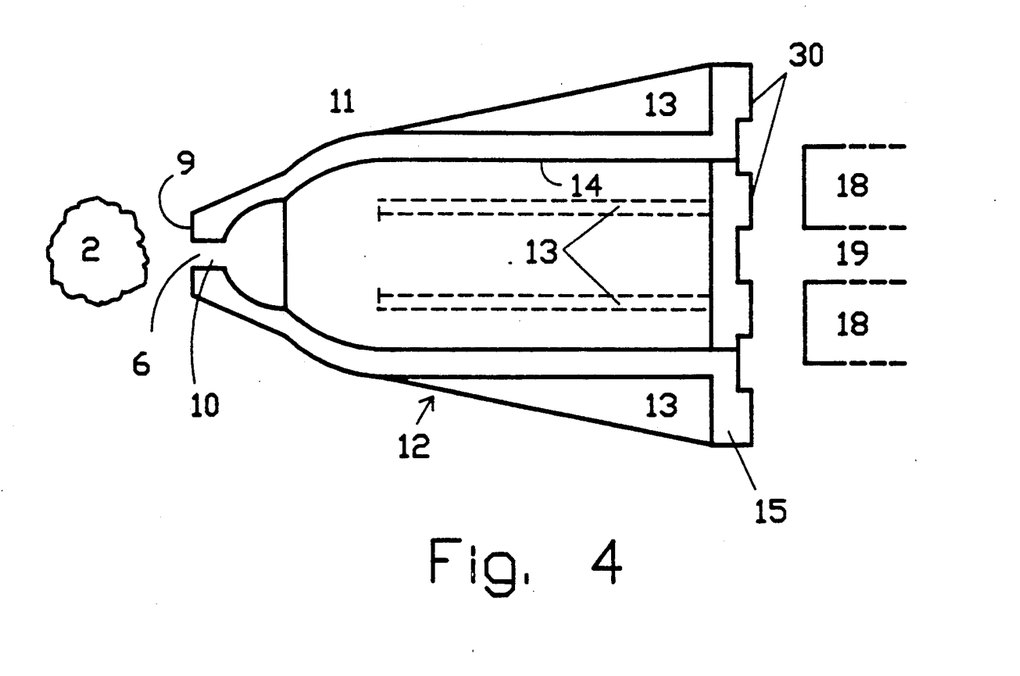
FIG. 4—illustrates in section one particular embodiment of the portion for contact between the instrument and the specimen.

FIG. 4 discloses a longitudinal section of the tip 11. The tip 11 is produced by injection of a material which may be chosen, for example, from PMMA-plexiglass, polypropylene or nylon. In any case it is desirable or even highly advisable that the material employed be transparent for it is important to be able to have a visible check whether the specimen has or has not been engaged in the tip under the action of the instrument.

It is as well to insist here upon the fact that this version of the instrument is designed essentially with the aim that the specimen shall not penetrate into the tip.

Besides the parts described with reference to FIG. 3 the tip likewise includes a trunk 12 upon which external fins 13 are arranged. The function of these fins is to give a hold for manipulation of the tip, especially when it is being fitted onto the portion 18 of the main body 16 intended for receiving it and when it is being disengaged from it. In fact partial movements of rotation to and fro along the longitudinal axis of the instrument are useful in these two operations. The cavity 14 inside the tip is shaped so as to ensure good cooperation with the corresponding portion 18 of the main body 16. Finally the tip ends in a crown 15 the shape of wich will be remarked upon later.

Figure 5:
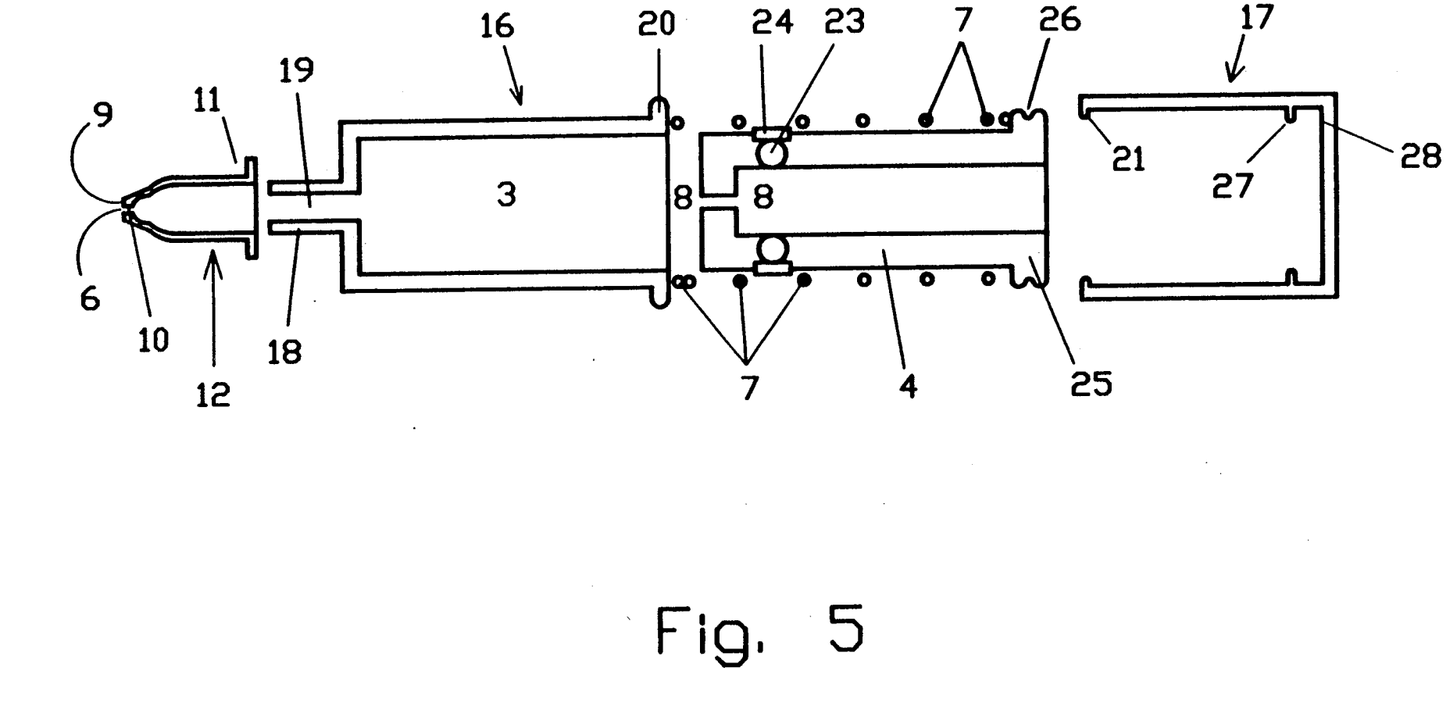
FIG. 5—is a section of the instrument in accordance with a version intended for repetitive use.

FIG. 5 shows the first non-disposable version of the instrument and in it a good number of the parts already described will be found again, such as the tip 11 with its contact area 9, the orifice 6 of the suction-ejection channel 10, the connecting trunk 12 with its cavity 14 and fins 13. The piston 4 and its microchannel 8 are likewise present. The recoil means 7 are also found again.

In this version it is found that the instrument is composed essentially of five parts, namely, a tip 11, a main body 16, a piston 4, a spring 7 and a hood 17. The main body 16 has a shape which recalls that of the main portion of a syringe and hence appears as a hollow cylinder. This main body may be produced from polypropylene according to known injection techniques. The main body has an outer diameter of about 12 mm and an inner diameter of about 10 mm. Its length is about 80 mm.

The connecting section 18 is to be observed, which is intended for cooperating with the cavity 14 in the tip 11. The dimensions of this section obviously have to be made to match those which have been chosen for the tip. Experiment shows, however, that a value of 3 mm may be kept for the outer diameter of the section 18 whereas an inner diameter of 1 mm may be chosen for the channel 19. The length of the connecting section 18 is about 8 mm. The temporary connection between the section 18 and the tip 11 is effected by means of a connector of LUER-LOCK type, which is a standard in the domain of medical instruments in particular.

At the end of the main body 16 remote from the tip 11 an annular lip 20 may be seen, which opens out outside the cylinder forming essentially the main body 16. The annular lip takes upon itself two distinct functions. It serves as a stop for the spring 7 and it equally plays the part of the male portion intended for cooperating with the reentrant annular lip 21 on the hood 17, which in turn plays the part of the female portion. The cooperation of the annular lips 20 and 21 is intended to integrate the main body 16 and the hood 17 in order to avoid the latter being ejected by the action of the spring 7. It may be stressed that the fit between the outer diameter of the annular lip 20 and the inner diameter of the hood 17 is chosen so as to tolerate the passage of air. The piston 4, likewise produced from polypropylene, has dimensions which have to be set very normally in relationship with those of the main body 16 with which it must cooperate. It appears in the form of a hollow cylinder one end of which is closed and forms the head. The length of the piston 4 is about 95 mm. Besides the microchannel 8 which has already been amply described the piston 4 likewise includes an airtight seal. This airtight seal consists of a toroidal "O-ring" seal 23 covered with a ring of TEFLON 24. It has in fact been found that an "O-ring" seal alone was not satisfactory inasmuch as the start of the movement is too abrupt, a disadvantage that the TEFLON ring alleviates in a quite conclusive manner, rendering the start of movement sufficiently gentle.

At the end remote from the head the piston 4 also has an outer annular lip 25 equipped with a circular catch groove 26. The outer lip 25 takes upon itself two distinct functions. On the one hand it serves as a stop for the other end of the spring 7 and on the other hand by its neck 26 it plays the part of the female portion intended for cooperating with the male portion represented by the inner lip 27 on the hood 17 in order to ensure integration of the piston 4 and the hood 17 which operates the piston 4. Finally the hood 17 of which the active portions have already been mentioned is also produced from polypropylene and occurs in the form of a hollow cylinder ending in a base 28. Its length is about 40 mm.

The operation of the instrument will now be described. If produced in accordance with the instructions for the dimensions as given above, the instrument has the appearance and proportions of a fountain pen.

The operator fits a tip onto the connector section 18 and grasps the instrument in the same way that he would grasp a ballpoint pen in order to actuate the pushbutton with his thumb. By means of his thumb the operator bears on the base 28 of the hood 17. Being integral with the hood thanks to the combined effect of the neck 26 and the lip 27, the piston compresses the spring 7 until it reaches the end of its travel. Whilst keeping the instrument in this configuration the operator approaches the tip 11 to the specimen until the contact area 9 touches the specimen. The operator then relaxes the pressure that he was exerting upon the base of the hood. Under the force of the spring the piston tends to recover its position of rest. The result is an effect of vaccum which makes the specimen adhere to the contact area 9 by suction and the operator takes advantage of it to withdraw the specimen immediately from the instrument upon or in which it is lying. As soon as the specimen is completely obstructing the orifice 6 in the suction channel 10 the return motion of the piston is in principle stopped. It is as this moment that the microchannel 8 intervenes to act as a calibrated air inlet. The deficit in volume resulting from the obstructing of the suction channel 10 in the tip is progressively made good by the supply of air passing through the microchannel 8. The piston can thus completely recover its position of rest. As was said at the start, specimens are small sticky masses. In fact they stick sufficiently to remain hanging on the tip even if the initial suction effect diminishes and then totally disappears whilst the piston is recovering its position of rest. The second part of the manipulation may then be carried out and the operator places the end of the instrument above the receiver and again bears upon the hood by means of his thumb. The air enclosed inside the main body is then expelled and the jet of air which results at the orifice 6 of the suction channel 10 is largely sufficient to drive off the specimen in spite of the minimum loss which the microchannel 8 allows, and the specimen falls into the receiver for presevation.

Figure 6:
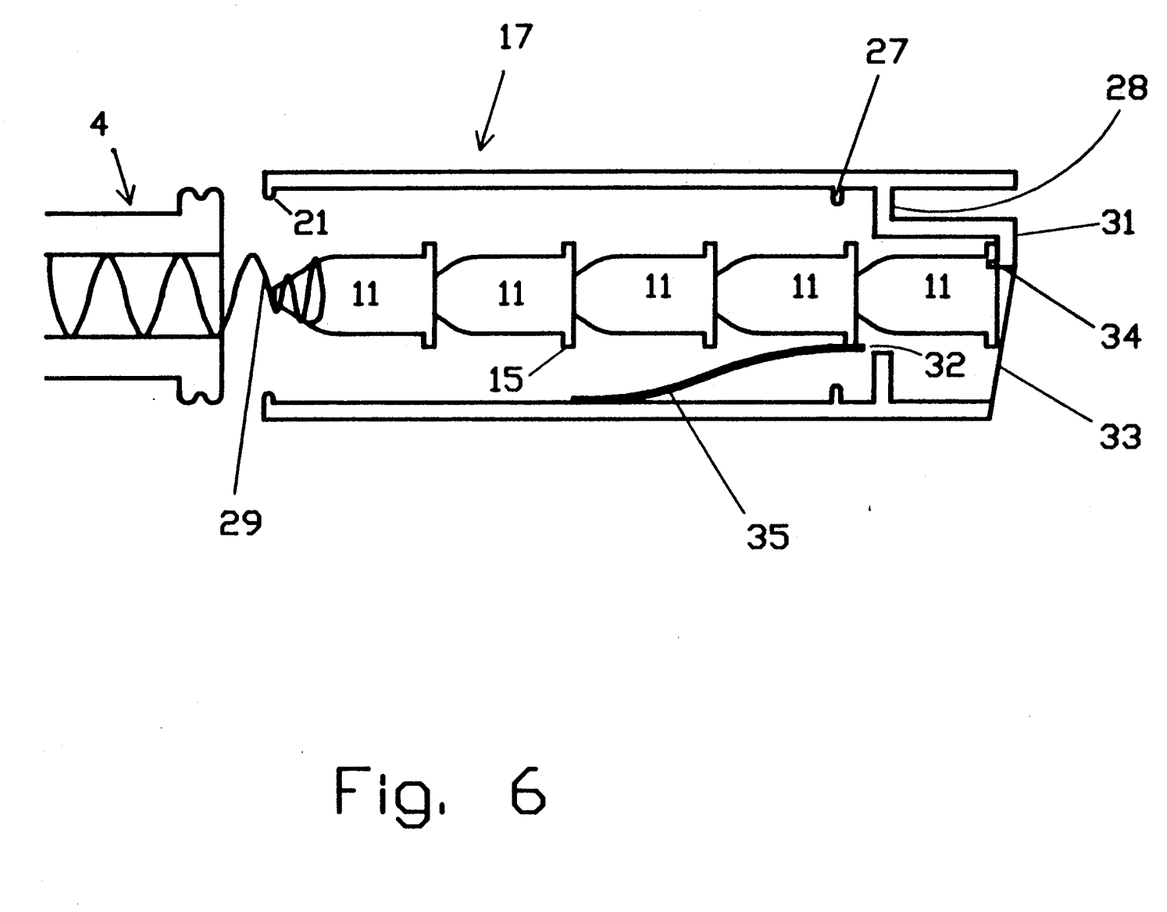
FIG. 6—illustrates the attachments which may be applied to the version of the instrument intended for repetitive use, in order to arrive at a more sophisticated second version.

With regard to FIG. 6 which represents a second variant upon the instrument in its version for repetitive use, it is suitable to present the instrument again as described with respect to FIG. 5, the only element undergoing modifications being the hood 17. According to this variant the hood 17 is equipped with reserve of tips 11 which occupies the body of the piston 4. This is moreover the reason why the piston 4 has been described as a cylinder closed at one end in FIG. 5; a piston as illustrated in FIG. 2 would have done the job quite as well.

In FIG. 6 a spring 29 is perceived again which is intended to push the column of tips 11 back against a small halfmoon retainer tongue 31. One end of the spring 29 bears against the inner face of the head of the piston 4. The other end of it bears against the last tip in the column. In this contact zone the diameter of the spring 29 is firstly squeezed in and then recovers its original diameter along a cone which embraces the general shape of the tip. The base 28 of the hood includes an outlet aperture 32 which opens into an oval cylindrical niche 33. This niche terminates in the small halfmoon retainer tongue 31 which includes a catch edge 34. This edge is intended for cooperating with the crown 15 on the tip so as to retain the latter. Turning back very briefly to FIG. 4 one finds that the crown on the tip includes castellations 30 which are provided in order to enable the user to get a grip when he is disengaging a tip with his finger by pushing up, which frees it from the catch edge 34. Thus freed, the tip leaves the reserve under the action of the spring 29. A small retainer tongue 35 pushes the column over so that the next tip in turn comes and takes up the waiting position, the crown 15 of the next tip being held by the cach edge 34. The small retainer tongue 35 enables the spring 29 ejecting the whole column at one go to be avoided.

Figures 7, 8:
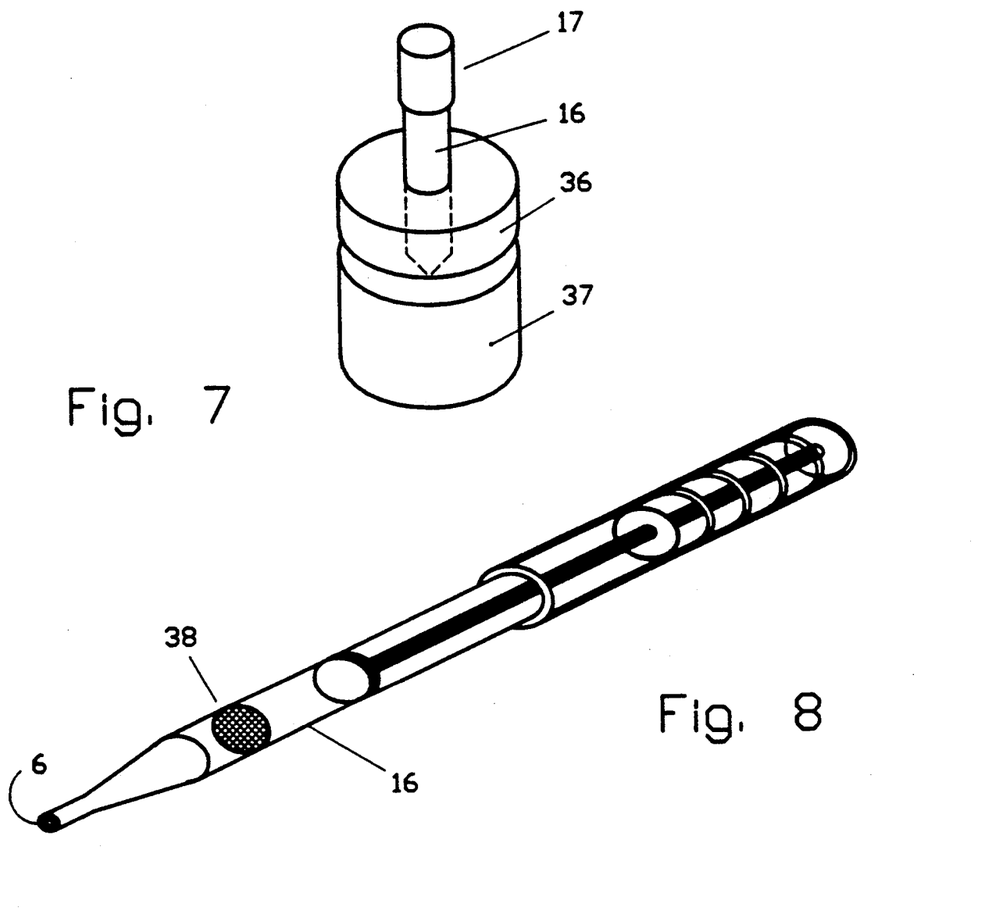
FIG. 7—illustrates a version of the instrument in which it is integral with the cap of the bottle.
FIG. 8—illustrates a version of the instrument in which the main body of it is provided with a grating.

In accordance with another variant represented in FIG. 7 the instrument as it has been described, in particular in FIGS. 1 to 5, is integrated with the cap 36 of the receiver 37 in which the specimen is to be deposited. Besides this special feature this variant is distinguished from the previous ones by the fact that on the one hand it is no longer necessarily required that the specimen should not penetrate into the instrument, neither on the other hand is it any longer absolutely necessary for the chamber of variable volume to have the service of a microchannel as a calibrated air inlet. The instructions given previously on the subject of the dimensions of the portion of the instrument for contact with the specimen and those concerning the microchannel have less importance in this variant.

Figure 9:
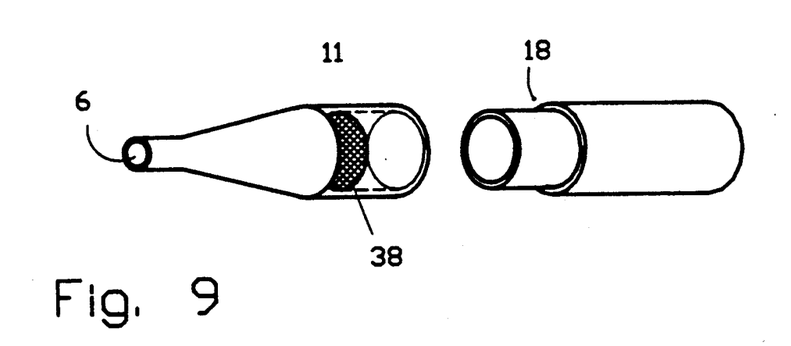
FIG. 9—illustrates a version of the instrument in which the tip is provided with a grating.

In accordance with yet another variant represented in FIGS. 8 to 9 the instrument is provided with a fine transverse grating 38 produced, for example, from carbon fibre, the aim of which is to prevent the specimen from penetrating into the instrument beyond the position fixed by the grating. In this variant it is assumed that the area of the orifice 6 is chosen so that the specimen can pass through the orifice and enter the instrument. In FIG. 8 the grating is positioned in the main body 16 of the instrument. This variant assumes that one instrument is employed for each specimen and that the whole instrument is sent to the laboratory for analysis. In FIG. 9 the grating is positioned in the tip so that it is solely the tips which are sent to the laboratory.

The advantages of the instrument in accordance with the invention are those of facilitating the manipulation of specimens whilst looking after them better than was the case hitherto and of looking after in the same fashion the instruments employed for taking these specimens. Again, the possibility of producing the instrument in disposable form enables existing installations for manufacture and injection to be employed which have huge productive capacities and render the cost of manufacure of he instrument as low as that of ordinary syringes. In its non-disposable version the adoption of the materials described enables sterilization of the instrument and offers, particularly thanks to a very soft airtight seal, appreciable comfort, in use. Finally the specimens are taken by specialists by means of extremely sophisticated and costly apparatus or instruments; the means of analysis are also at the peak of technical perfection but the unavoidable stage which consists in manipulating the specimen is left to "D.I.Y. System". The pneumatic transfer of the specimens which is made possible by the instrument in accordance with the invention cures this anachronistic weakness and enables it to be avoid that valuable apparatus remain immobilized or are damaged because of an operation of simple handing which is often difficult but always indispensable.

I claim:

1. An instrument for the handling of biopsies and specimens, comprising:
    a syringe cylinder having a first and a second end, and defining a chamber of variable volume therebetween;
    a piston moveable within the chamber to vary the volume of the chamber between a maximum volume when the piston is moved to the first end of the cylinder and a minimum volume when the piston is moved to the second end of the cylinder;
    a means of recoil at the first end of the cylinder biasing the piston toward the first end of the cylinder;
    a contact means at the second end of the cylinder for making contact with biopsies and specimens, including a contact area and a channel for air flow communicating the contact area with the chamber; and
    a microchannel means, including at least one calibrated air channel permanently communicating the chamber with the atmosphere, providing a controlled flow of air into and out of the chamber such that when the piston is at the second end of the cylinder and the contact means is obturated by biopsies or specimens a sufficient volume of air flows into the chamber through the microchannel means to permit the means of recoil to bias the piston toward the first end of the cylinder, and such that when the piston is more rapidly moved from the first and to the second end of the cylinder an insufficient volume of air flows out of the chamber through the microchannel means to prevent the volume of air flowing out of the chamber through the channel for air flow from ejecting the biopsies or specimens from the contact area.

2. The instrument for the handling of biopsies and specimens of claim 1 wherein the microchannel means includes a calibrated air channel communicating the chamber at its minimum volume with the atmosphere.

3. The instrument for the handling of biopsies and specimens of claim 2 wherein the microchannel means includes a calibrated air channel through the piston communicating the chamber at its minimum volume with the atmosphere.

* * * * *

UNITED STATES PATENT AND TRADEMARK OFFICE
CERTIFICATE OF CORRECTION

PATENT NO. : 5,255,688

DATED : October 26, 1993

INVENTOR(S) : Rene Gilliard

It is certified that error appears in the above-identified patent and that said Letters Patent is hereby corrected as shown below:

In column 8, line 45, change "and" to -- end --.

Signed and Sealed this

Nineteenth Day of April, 1994

Attest:

BRUCE LEHMAN

*Attesting Officer*   *Commissioner of Patents and Trademarks*